(12) United States Patent
Gold

(10) Patent No.: US 8,322,485 B1
(45) Date of Patent: Dec. 4, 2012

(54) SYSTEMS AND METHODS FOR REDUCTION OF NOISE DURING SLEEP

(76) Inventor: Eric Gold, Martinsville, NJ (US)

( * ) Notice: Subject to any disclaimer, the term of this patent is extended or adjusted under 35 U.S.C. 154(b) by 0 days.

(21) Appl. No.: 13/222,551

(22) Filed: Aug. 31, 2011

(51) Int. Cl.
*H04R 25/00* (2006.01)
(52) U.S. Cl. ...................................... 181/129
(58) Field of Classification Search ........... 181/129, 181/128, 126; 2/171; 128/848; 5/636
See application file for complete search history.

(56) References Cited

U.S. PATENT DOCUMENTS

| | | | |
|---|---|---|---|
| 3,621,488 A * | 11/1971 | Gales | ............... 381/372 |
| 4,192,029 A | 3/1980 | Bond | |
| 4,305,168 A | 12/1981 | Holter et al. | |
| 4,349,925 A | 9/1982 | Macomber | |
| 4,707,031 A | 11/1987 | Meistrell | |
| 5,127,117 A | 7/1992 | Bridges | |
| 6,000,401 A | 12/1999 | Herrick | |
| 6,003,177 A | 12/1999 | Ferris | |
| 6,088,836 A * | 7/2000 | de Cordova | ................ 2/171 |
| D465,234 S * | 11/2002 | Gordon | ............. D16/301 |
| 6,607,245 B1 | 8/2003 | Scher | |
| 6,651,256 B1 * | 11/2003 | Swift | ................ 2/171 |
| 6,698,432 B2 | 3/2004 | Ek | |
| D489,749 S * | 5/2004 | Landvik | .......... D16/301 |
| 6,817,049 B1 | 11/2004 | Hall | |
| 7,004,545 B2 | 2/2006 | Miller | |
| 7,203,983 B1 | 4/2007 | Reeves et al. | |
| 7,428,763 B2 | 9/2008 | Hightower | |
| D614,901 S | 5/2010 | Welch | |
| D615,453 S | 5/2010 | Spears | |
| 7,740,318 B2 | 6/2010 | Funke, III et al. | |
| 7,832,802 B2 | 11/2010 | Ehlers et al. | |
| 2004/0124685 A1 | 7/2004 | Buch | |
| 2006/0179572 A1 | 8/2006 | Rubio | |
| 2008/0189863 A1 | 8/2008 | Zappas | |
| 2008/0216244 A1 | 9/2008 | Minton | |
| 2009/0307846 A1 * | 12/2009 | Eura et al. | ................ 5/636 |
| 2010/0102604 A1 | 4/2010 | Barnes et al. | |
| 2011/0031799 A1 | 2/2011 | DeJoode | |

* cited by examiner

*Primary Examiner* — Forrest M Phillips
(74) *Attorney, Agent, or Firm* — Mintz Levin Cohn Ferris Glovsky and Popeo, P.C.

(57) ABSTRACT

A noise reduction system for attachment to a pillow having a top surface is disclosed, wherein a head of a user can be configured to be placed on the top surface of the pillow. The system includes a plurality of support bands, each having a distal end and a proximate end, wherein the distal end of each of the plurality of support bands is configured to be coupled to the pillow and a pad configured to be coupled to each proximate end of each of the plurality of support bands. Upon coupling of the distal end of each of the plurality of support bands to the pillow, the pad is configured to be disposed above the top surface of the pillow at a predetermined height. The head of the user is configured to be placed between the top surface of the pillow and the pad, wherein the pad is configured to cover an ear of the user to reduce noise perceived by the ear of the user.

17 Claims, 3 Drawing Sheets

SYSTEMS AND METHODS FOR REDUCTION OF NOISE DURING SLEEP

TECHNICAL FIELD

The present invention relates to reducing levels of outside noise during sleep. Specifically, the present invention relates to a device that is configured to be attached to a pillow and is further configured to suppress or reduce outside noise during sleep.

BACKGROUND

Sleep is a naturally recurring state characterized by reduced or absent consciousness, relatively suspended sensory activity, and inactivity of nearly all voluntary muscles. Sleep is also a heightened anabolic state, accentuating the growth and rejuvenation of the immune, nervous, skeletal and muscular systems. Sleep is often thought to help conserve energy, regenerate body strength, allow the body to heal itself and/or recover from injury or illness, or simply permits one to rest. Thus, getting a right amount of uninterrupted sleep can be paramount to one's health and ability to function. Some scientific studies suggested that an adult should get between seven to eight hours of sleep every night to maintain a healthy lifestyle. It has also been shown that a reduced amount of sleep leads to an increased risk of motor vehicle accidents, an increase in body mass index, i.e., a greater likelihood of obesity due to an increased appetite caused by sleep deprivation, an increased risk of diabetes and heart problems, an increased risk for psychiatric conditions including depression and substance abuse, a decreased ability to pay attention, react to signals or remember new information.

Sleep interruption results in a reduced amount of sleep that one may be getting, and thus may cause to the above described issues. One of the common causes of sleep interruption is noise that may be present in the area surrounding one's sleeping quarters or location. Such noise can be a street noise (e.g., cars driving by, blaring sirens of emergency vehicles, dogs barking, etc.), snoring, noisy neighbors, etc. and/or any combination of the above. To prevent sleep interruption, various solutions have been implemented. One includes ear plugs that one can put into his/her ears prior to going to sleep. However, ear plugs can be bulky, generate some discomfort or even painful for the user, and have to be replaced often for sanitary reasons, thereby making them very costly. Other solutions included white noise music and/or sleep machines that generate various soothing sounds. However, while capable of drowning some noise, such machines/music are still incapable of taking out other persistent noises (e.g., snoring, street noise, noisy neighbors), and hence, do not present a viable solution. Others have uses pouch-type pillows and/or straps that wrap one's head in a pillow to block outside noise. These solutions, while may be somewhat effective in reducing the noise, are not designed to allow their user to move freely during sleep while still blocking the desired amount of noise. Also, such solutions may increase one's head temperature as well as provide a greater risk of suffocation in the event that the user turns in an undesired way.

Thus, there is a need for a solution that is capable of providing desired noise suppression or reduction during one's sleep that allows its user to freely move around during sleep while providing the requisite noise suppression/reduction.

SUMMARY

In some embodiments, the current subject relates to a noise reduction system for attachment to a pillow having a top surface, wherein a head of a user of the system can be configured to be placed on the top surface of the pillow. The system includes a plurality of support bands, each having a distal end and a proximate end, wherein the distal end of each of the plurality of support bands is configured to be coupled to the pillow and a pad configured to be coupled to each proximate end of each of the plurality of support bands. Upon coupling of the distal end of each of the plurality of support bands to the pillow, the pad is configured to be disposed above the top surface of the pillow at a predetermined height. The head of the user is configured to be placed between the top surface of the pillow and the pad, wherein the pad is configured to cover an ear of the user to reduce noise perceived by the ear of the user.

In some embodiments, the current subject matter is configured to include at least one of the following optional features. The support bands are configured to be permanently coupled to the pillow, wherein the support bands, the pad, and the pillow are configured to form an integral structure. The support bands are configured to be detachably coupled to the pillow using at least one securing mechanism, wherein the at least one securing mechanism is configured to be disposed at the distal end of each of the plurality of support bands. The at least one securing mechanism includes at least one of the following: straps, strings, snaps, snap-ons, VELCRO®, hooks, magnets, loops, and clips. At least one of the pad, the plurality of support bands, and the pillow is configured to be manufactured from the same material. The material includes at least one of the following: a TEMPURPEDIC® material, a memory foam material, a cloth, a synthetic, a flexible plastic material, and any various combinations of materials. The pad is configured to be manufactured from a noise reducing material. The pad is configured to have a predetermined thickness, wherein the predetermined thickness depends on a level of noise reduction desired by the user. Each support band in the plurality of support bands is configured to have an elastic or spring-like property and further configured to pull the pad toward the ear of the user when the head of the user is resting on the top surface of the pillow. The pad is configured to have a flat shape. The pad is configured to have a curved shape. A length of each support band in the plurality of support bands is configured to depend on a size of the head of the user. The length of each support band in the plurality of support bands is configured to be adjustable. The pad and each support band in the plurality of support bands are configured to be detachably coupled. Upon coupling of each support band in the plurality of support bands to the pillow, an open space is created between the top surface of the pillow and the pad, thereby allowing insertion of the head of the user between the top surface of the pillow and the pad and further allowing movement of the head of the user between the top surface of the pillow and the pad. At least one support band in the plurality of support bands has a different length than at least another support band in the plurality of support bands.

In some embodiments, the current subject matter relates to a method of reducing perception of noise during sleep. The method includes providing a noise reduction system for attachment to a pillow having a top surface described above, coupling of the distal end of each of the plurality of support bands to the pillow, wherein the coupling results in the pad being disposed above the top surface of the pillow at a predetermined height, placing the head of the user between the top surface of the pillow and the pad, and, using the pad, covering an ear of the user, thereby reducing noise perceived by the ear of the user.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

Some embodiments of the current subject matter relate to systems and methods for reducing and/or suppressing noise during sleep. In particular, some embodiments of the current subject matter relate to a pillow attachment system that can be configured to suppress and/or reduce noise as desired.

Figure 1:
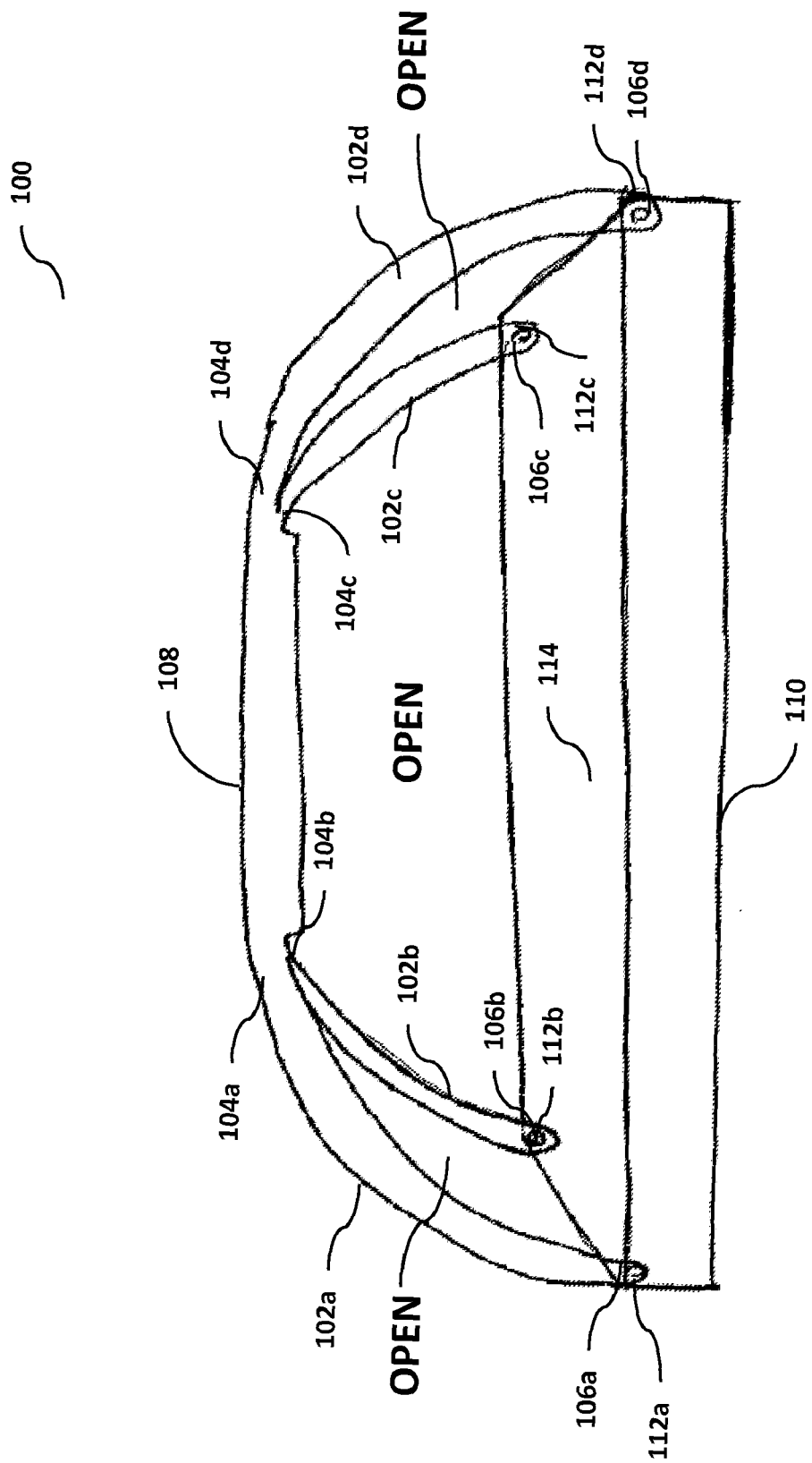
FIG. 1 illustrates an exemplary system for reducing perception of noise during sleep, according to some embodiments of the current subject matter.

FIG. 1 illustrates an exemplary system 100 for suppressing and/or reducing noise during sleep, according to some embodiments of the current subject matter. The system 100 can include a plurality of support arches (or support bands, straps, belts, securing mechanisms, etc.) 102 (a, b, c, d) that include respective proximate ends 104 (a, b, c, d) and respective distal ends 106 (a, b, c, d). The proximate ends 104 can be configured to be coupled to a pad (or a covering, a layer, or a jacket, etc.) 108. The distal ends 106 can be configured to be coupled to a pillow 110. As illustrated in FIG. 1, the distal ends 106 of the support arches 102 can be coupled to respective corners 112 (a, b, c, d) of the pillow. In some embodiments, the support arches 102 can be coupled to any portion of the pillow (e.g., corners, edges, top surface, bottom surface, etc., and/or any combination of the above) and/or pillow case that is put over the pillow.

The support arches 102 can be configured to be permanently coupled to the pillow 110, thereby forming an integral structure with the pad 108. Alternatively, the support arches 102 can be configured to be detachably coupled to the pad 108. Further, the support arches 102 can be configured to be detachably coupled to the pillow 110. Alternatively, the support arches 102 can be configured to be permanently coupled to the pillow, thereby forming an integral structure with the pillow 110.

In some embodiments, the support arches 102, the pad 108, and the pillow 110 can be configured to be manufactured from the same material, e.g., TEMPURPEDIC® material, and/or any other desired material. In some embodiments, the support arches 102, the pad 108 and/or the pillow 110 can be manufactured from different materials.

The pad 108 can be configured to have an arcuate, concave, or a curved shape. In some embodiments, the pad 108 can be configured to have a flat shape. The support arches 102 can be configured to have a curved shape, or, alternatively, they can be straight, as shown in FIG. 1.

The support arches 102 and the pad 108 can be configured to form a support structure (for example, in a form of a canopy) that is configured to be disposed above a top surface 114 of the pillow 110 once the support arches 102 are coupled to the pillow 110. In order to utilize the system 100, a user can attach the system 100 (if it is not permanently attached) to the pillow 110. The system 100 attached to the pillow 110 can be placed on a bed with the system 100 being disposed above the top surface 112 of the pillow 110. Then, the user can place user's head between a bottom surface of the pad 108 and the top surface 114 of the pillow 110 (indicated by "OPEN" in FIG. 1). Once the user has turned to his/her side on the pillow, one of the user's ears will become exposed while the other ear is displaced against the top surface of the pillow. The pad 108 can be configured to cover the entire exposed ear of the user, thereby blocking and/or reducing extraneous noise that may be present in the vicinity of the user's sleeping quarters. In some embodiments, the support arches 102 can be configured to have some elasticity and/or spring-like qualities and can be configured to pull the pad 108 toward the user's exposed ear, thereby snuggly covering that ear.

The system 100 can be configured to allow the user to turn, for example from side to side, while the user is sleeping. If the user desires to turn, the support arches 102 can be configured to permit user's head movement on the pillow and once the user has settled on the top surface 114 of the pillow on the user's other side, the support arches 102, in view of its elastic and/or spring-like features, can be configured to pull the pad 108 toward the user's now-exposed ear, thereby blocking, suppressing or otherwise reducing extraneous noise allowing the user to enjoy comfortable and quiet sleep.

The components (e.g., support arches 102, pad 108, etc.) of the system 100 can have different sizes for any size users' heads (e.g., adult, child, teenager, etc., all of which can be extra large, large, medium, small, extra small, etc.). Thus, a user can obtain system 100 based on the size of user's head. In some exemplary embodiments, the pad 108 can have any desired size and can be, for example a pad having a size of approximately 16 inches by approximately 16 inches. The support arches 102 can also have any desired sizes and can be, for example, approximately 12 inches in length and approximately 2 inches in width. In some embodiments, the support arches can also have different lengths (thereby allowing a head insertion opening (e.g., between arches 102a and 102d in FIG. 1) or a front opening in the system 100 to be larger than the opening in the back of the system 100 (i.e., where the user does not insert his/her head (i.e., between arches 102b and 102c))). In some embodiments, the pad 108 can be disposed approximately 12 inches above the top surface 114 of the pillow 110.

In some embodiments, the thickness of the pad 108 (and/or the arches 102) can vary according to a desired level of noise suppression, blockage, or reduction. For greater noise reduction, the pad 108 (and/or the arches 102) can be made thicker. For lesser noise reduction, the pad 108 (and/or the arches 102) can be made thinner In addition to suppressing, blocking and/or reducing noise for the user during sleep, the system 100 can be configured to provide proper air circulation inside the system 100, thereby preventing user suffocation or overheating of the user's head. Additionally, the system 100 permits the user to move freely inside the system 100.

Figure 2:
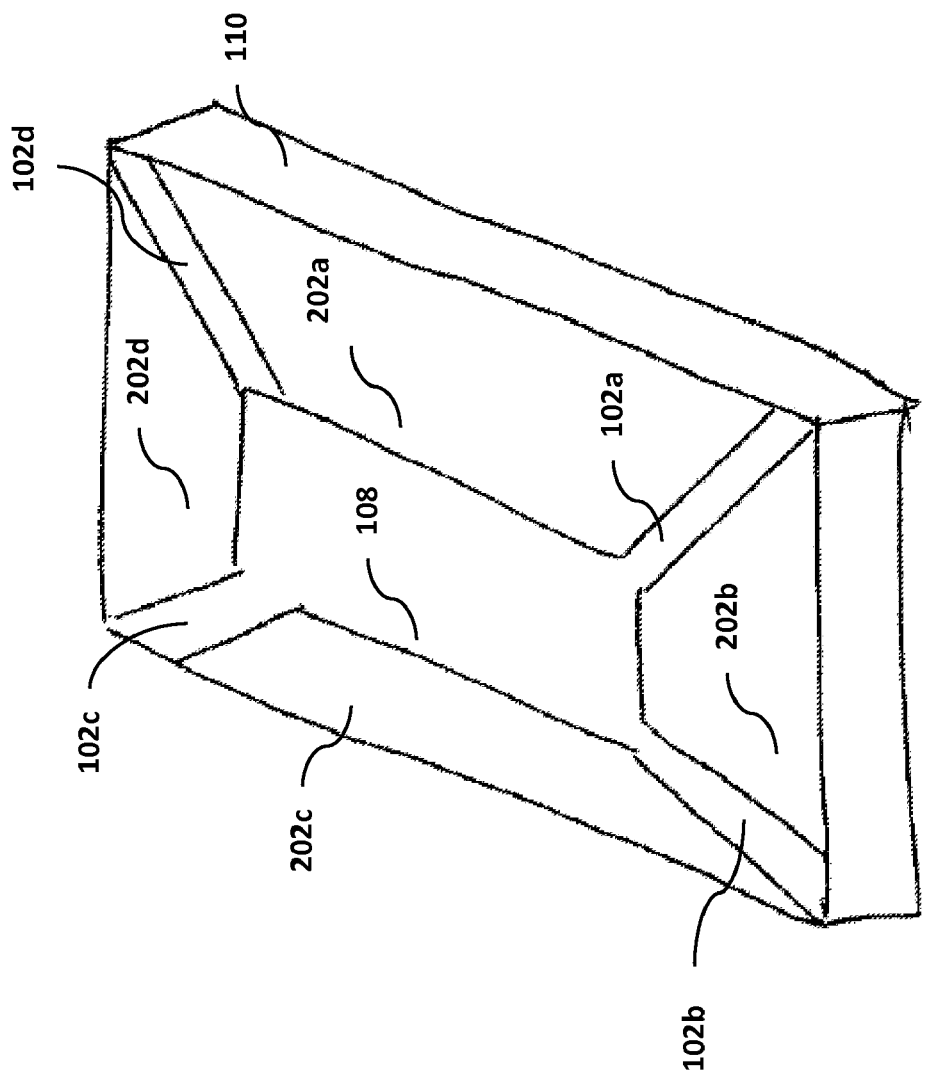
FIG. 2 is a top perspective view of the system shown in FIG. 1.

FIG. 2 is a top perspective view of the system 100. As discussed above, the system 100 can be coupled to the pillow 100 at its corners 112. Once the system 100 is coupled to the pillow 110, the system is configured to include openings 202 (a, b, c, d) disposed between the arches 102 (a, b, c, d). For example, the opening 202a is disposed between arches 102a and 102d. The opening 202b is disposed between arches 102a and 102b. The opening 202c is disposed between arches 102b and 102c. The opening 202d is disposed between arches 102c and 102d. The openings 202 can have different sizes and may depend on the size and shape of the pillow 110 and/or length of the arches 102. In some embodiments, the system 100 can be configured to be coupled to any size and/or shape pillow 110. This can be useful when the user is travelling.

Figure 3:
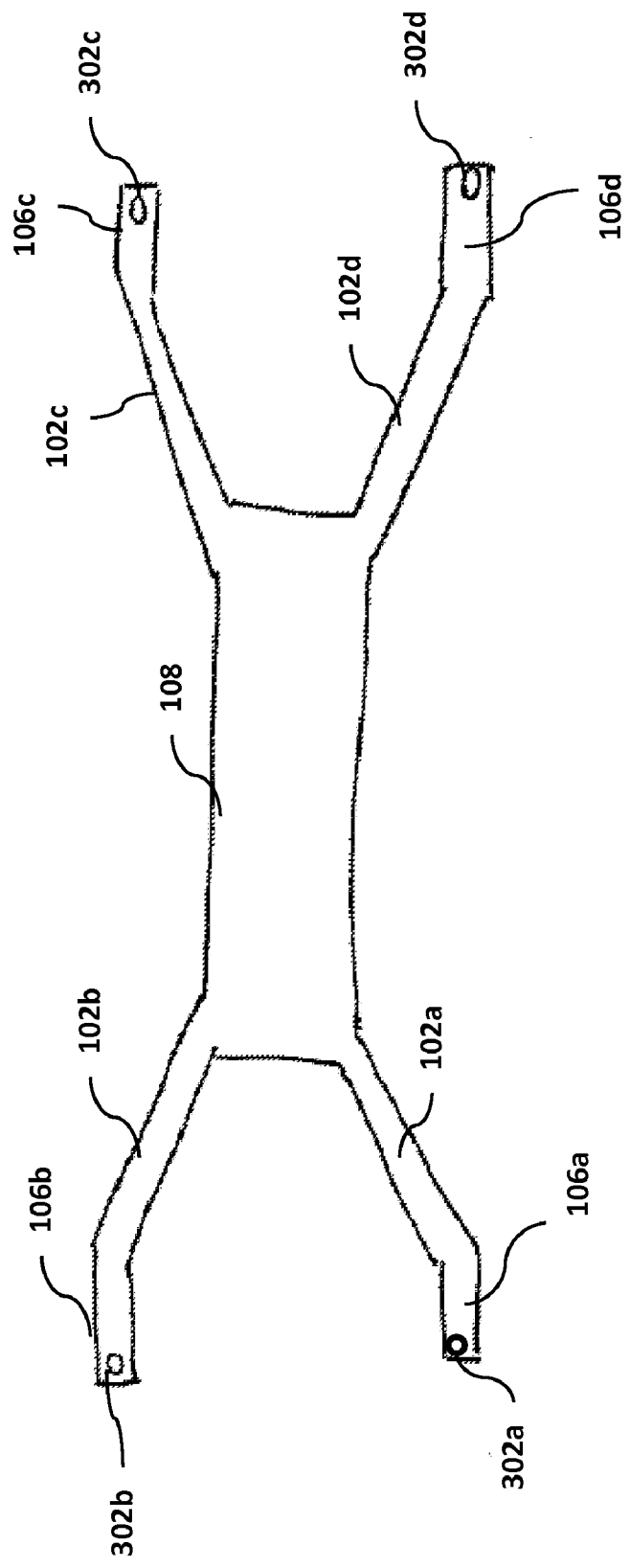
FIG. 3 is another view of the system shown in FIG. 1.

In some embodiments, the arches 102 can be configured to including coupling mechanisms 302 (a, b, c, d) at its distal ends 106 (a, b, c, d), as shown in FIG. 3. The coupling mechanisms 302 can include at least one of the following:

straps, strings, snaps, snap-ons, VELCRO®, hooks, magnets, loops, clips, and/or any other devices that can be configured to couple the system 100 either permanently or temporarily to the pillow 110. The pillow 100 can be configured to include mechanisms at its corners 112 that can be configured to mate with the mechanisms 302. In some embodiments, the system 100 can be configured to attach to any pillow whether or not it includes mating attachment mechanisms. In alternate embodiments, the system 100 can be made integral with the pillow 110 (e.g., the pad 108, the arches 102 and the pillow 110 can form a single unit). The system 100 can be further configured to be coupled to any size and/or shape pillow, including a king size pillow, a queen size pillow, a standard size pillow, a twin size pillow, a European type pillow, a square pillow, a rectangular pillow, a round pillow, an irregular shape pillow, and/or any other type, size and/or shape pillow.

In some embodiments, the current subject relates to a noise reduction system for attachment to a pillow having a top surface, wherein a head of a user of the system can be configured to be placed on the top surface of the pillow. The system includes a plurality of support bands, each having a distal end and a proximate end, wherein the distal end of each of the plurality of support bands is configured to be coupled to the pillow and a pad configured to be coupled to each proximate end of each of the plurality of support bands. Upon coupling of the distal end of each of the plurality of support bands to the pillow, the pad is configured to be disposed above the top surface of the pillow at a predetermined height. The head of the user is configured to be placed between the top surface of the pillow and the pad, wherein the pad is configured to cover an ear of the user to reduce noise perceived by the ear of the user.

In some embodiments, the current subject matter is configured to include at least one of the following optional features. The support bands are configured to be permanently coupled to the pillow, wherein the support bands, the pad, and the pillow are configured to form an integral structure. The support bands are configured to be detachably coupled to the pillow using at least one securing mechanism, wherein the at least one securing mechanism is configured to be disposed at the distal end of each of the plurality of support bands. The at least one securing mechanism includes at least one of the following: straps, strings, snaps, snap-ons, VELCRO®, hooks, magnets, loops, and clips. At least one of the pad, the plurality of support bands, and the pillow is configured to be manufactured from the same material. The material can be TEMPURPEDIC® material, memory foam material, cloth, synthetic, flexible plastic material, and/or any other material and/or any various combinations of materials. The pad is configured to be manufactured from a noise reducing material. The pad is configured to have a predetermined thickness, wherein the predetermined thickness depends on a level of noise reduction desired by the user. Each support band in the plurality of support bands is configured to have an elastic or spring-like property and further configured to pull the pad toward the ear of the user when the head of the user is resting on the top surface of the pillow. The pad is configured to have a flat shape. The pad is configured to have a curved shape. A length of each support band in the plurality of support bands is configured to depend on a size of the head of the user. The length of each support band in the plurality of support bands is configured to be adjustable. The pad and each support band in the plurality of support bands are configured to be detachably coupled. Upon coupling of each support band in the plurality of support bands to the pillow, an open space is created between the top surface of the pillow and the pad, thereby allowing insertion of the head of the user between the top surface of the pillow and the pad and further allowing movement of the head of the user between the top surface of the pillow and the pad. At least one support band in the plurality of support bands has a different length than at least another support band in the plurality of support bands.

In some embodiments, the current subject matter relates to a method of reducing perception of noise during sleep. The method includes providing a noise reduction system for attachment to a pillow having a top surface described above, coupling of the distal end of each of the plurality of support bands to the pillow, wherein the coupling results in the pad being disposed above the top surface of the pillow at a predetermined height, placing the head of the user between the top surface of the pillow and the pad, and, using the pad, covering an ear of the user, thereby reducing noise perceived by the ear of the user.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A noise reduction system for attachment to a pillow, the pillow having a top surface, wherein user places a head of the user on the top surface of the pillow, the noise reduction system comprising:
   a plurality of support bands, each having a distal end and a proximate end, wherein the distal end of each of the plurality of support bands is configured to be coupled to the pillow;
   a noise reducing pad being separate from the pillow and having each proximate end of each of the plurality of support bands coupled to the pad;
   the pad, upon each distal end of each of the plurality of support bands being coupled to the pillow, is configured to be disposed above the top surface of the pillow at a predetermined height;
   wherein the user places the head of the user on the top surface of the pillow and between the top surface of the pillow and the pad, so that the pad covers one ear of the user to reduce noise perceived by the ear of the user.

2. The system according to claim 1, wherein the support bands are configured to be permanently coupled to the pillow, wherein the support bands, the pad, and the pillow are configured to form an integral structure.

3. The system according to claim 1, wherein the support bands are configured to be detachably coupled to the pillow using at least one securing mechanism, wherein the at least one securing mechanism is configured to be disposed at the distal end of each of the plurality of support bands.

4. The system according to claim 3, wherein the at least one securing mechanism includes at least one of the following: straps, strings, snaps, snap-ons, VELCRO®, hooks, magnets, loops, and clips.

5. The system according to claim 1, wherein at least one of the pad, the plurality of support bands, and the pillow is configured to be manufactured from the same material.

6. The system according to claim 5, wherein the material includes at least one of the following: a TEMPURPEDIC® material, a memory foam material, a cloth, a synthetic, a flexible plastic material, and any various combinations of materials.

7. The system according to claim 1, wherein the pad is configured to be manufactured from a noise reducing material.

8. The system according to claim 1, wherein the pad is configured to have a predetermined thickness, wherein the predetermined thickness depends on a level of noise reduction desired by the user.

9. The system according to claim 1, wherein each support band in the plurality of support bands is configured to have an elastic or spring-like property and further configured to pull the pad toward the ear of the user when the head of the user is resting on the top surface of the pillow.

10. The system according to claim 1, wherein the pad is configured to have a flat shape.

11. The system according to claim 1, wherein the pad is configured to have a curved shape.

12. The system according to claim 1, wherein a length of each support band in the plurality of support bands is configured to depend on a size of the head of the user.

13. The system according to claim 12, wherein the length of each support band in the plurality of support bands is configured to be adjustable.

14. The system according to claim 1, wherein the pad and each support band in the plurality of support bands are configured to be detachably coupled.

15. The system according to claim 1, wherein upon coupling of each support band in the plurality of support bands to the pillow, an open space is created between the top surface of the pillow and the pad, thereby allowing insertion of the head of the user between the top surface of the pillow and the pad and further allowing movement of the head of the user between the top surface of the pillow and the pad.

16. The system according to claim 1, wherein at least one support band in the plurality of support bands has a different length than at least another support band in the plurality of support bands.

17. A method of reducing perception of noise during sleep, comprising:
    providing a noise reduction system for attachment to a pillow, the pillow having a top surface, wherein the noise reduction system includes
        a plurality of support bands, each having a distal end and a proximate end, wherein the distal end of each of the plurality of support bands is configured to be coupled to the pillow;
        a noise reducing pad being separate from the pillow and having_each proximate end of each of the plurality of support bands coupled to the pad;
    coupling each distal end of each of the plurality of support bands to the pillow, wherein the coupling results in the pad being disposed above the top surface of the pillow at a predetermined height;
    placing the head of the user between the top surface of the pillow and the pad; and,
    using the pad, covering an ear of the user, thereby reducing noise perceived by the ear of the user.

\* \* \* \* \*